United States Patent [19]

Krishnamurthy

[11] Patent Number: 5,571,926
[45] Date of Patent: Nov. 5, 1996

[54] ONE-STEP PROCESS FOR PREPARATION OF N-(4-SUBSTITUTED PYRAZOLYL) AMIDINES AS INTERMEDIATES IN PT-COUPLER SYNTHESIS

[75] Inventor: Sundaram Krishnamurthy, Rochester, N.Y.

[73] Assignee: Eastman Kodak Company, Rochester, N.Y.

[21] Appl. No.: 614,610

[22] Filed: Oct. 2, 1995

Related U.S. Application Data

[63] Continuation of Ser. No. 83,763, Jun. 30, 1993, abandoned.

[51] Int. Cl.⁶ .................................................. C07D 231/38
[52] U.S. Cl. ..................... 548/371.7; 548/364.7
[58] Field of Search ............................ 548/371.7

[56] References Cited

U.S. PATENT DOCUMENTS

| | | |
|---|---|---|
| 4,753,870 | 6/1988 | Takada et al. . |
| 4,814,262 | 3/1989 | Sugita et al. . |
| 4,880,733 | 11/1989 | Kaneko . |
| 4,945,034 | 7/1990 | Tanji et al. . |

FOREIGN PATENT DOCUMENTS

| | | |
|---|---|---|
| 0381183 | 8/1990 | European Pat. Off. . |
| 0397050 | 11/1990 | European Pat. Off. . |

OTHER PUBLICATIONS

Sambaiah et al, *Synthesis*, (1990) pp. 422–424.

*Primary Examiner*—Robert W. Ramsuer
*Attorney, Agent, or Firm*—Arthur E. Kluegel

[57] ABSTRACT

In the production of 1H-pyrazolo[1,5-b] [1,2,4]triazole couplers, substituted 3-amino-pyrazole compounds add to suitable organic nitriles in the presence of an acidic condensing agent such as aluminum chloride, stannic chloride or boron trifluoride to directly produce desired amidine intermediates in good yields, avoiding the generation of moisture sensitive intermediate imidate esters. Moreover, the availability of oxidation techniques to convert amidines to 1H-pyrazolo[1,5-b] [1,2,4]triazole couplers in a single step makes it possible to produce these couplers in a total of two steps compared to conventional multi-step synthetic schemes.

6 Claims, No Drawings

ONE-STEP PROCESS FOR PREPARATION OF N-(4-SUBSTITUTED PYRAZOLYL) AMIDINES AS INTERMEDIATES IN PT-COUPLER SYNTHESIS

This application is a continuation, of application Ser. No. 08/083,763, filed Jun. 30, 1993 now abandoned.

FIELD OF THE INVENTION

This invention relates to photographic couplers, particularly to pyrazolotriazole magenta couplers, preferably to 1-H-pyrazolo[1,5-b] [1,2,4]triazole magenta couplers of class 218 (hereafter PT couplers). More specifically, it relates to a process for the one-step synthesis of a key intermediate in PT coupler synthesis by the direct addition of the aminopyrazoles to suitable organic nitriles in the presence of a condensing agent.

BACKGROUND OF THE INVENTION

Pyrazolotriazole dye-forming magenta couplers are well known in the color image-forming coupler art. Such couplers provide magenta dyes with superior dye light stability. This class of couplers often require multi-step synthetic sequences, involving moisture sensitive intermediates such as imidates, resulting in lower overall yields. The present invention relates to a process of preparing N-(4-substituted pyrazolyl)amidines (I) which are useful key intermediates in the preparation of PT coupler compounds of the formula (II).

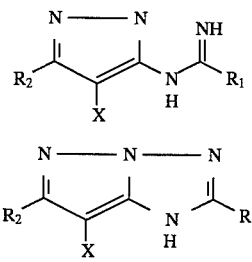

Formula (II) represents pyrazolotriazole compounds which are PT dye-forming magenta couplers employed in photographic silver halide materials. In the above formulae (I) and (II), X is a coupling-off group and $R_1$ and $R_2$ are independently hydrogen or a coupler substituent known in the photographic art which does not adversely affect the desired properties of the coupler. Pyrazolotriazoles of formula (II) can be obtained from the amidines of formula (I) by methods known in the art.

The methods known in the art for the synthesis of amidines involve the reaction of the organic nitrile with a suitable alcohol in the presence of anhydrous hydrogen chloride to form the imidate ester, which on subsequent reaction with a 3-amino-4-substituted-5-alkylpyrazole furnished the desired amidine.

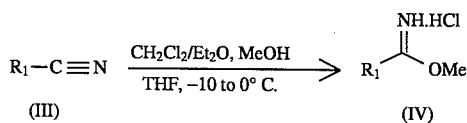

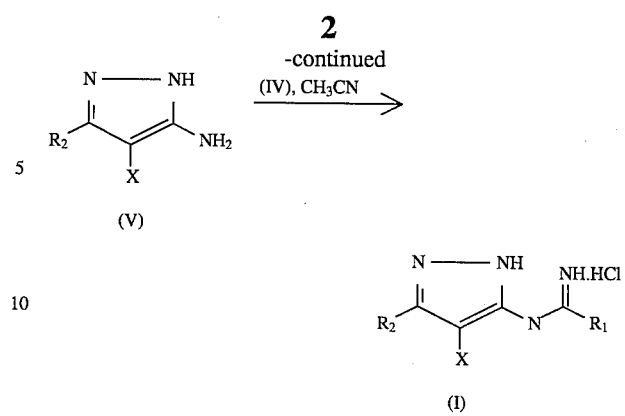

Unfortunately, this process involves the isolation and manipulation of rather unstable and highly moisture sensitive intermediate imidate esters (IV).

SUMMARY OF THE INVENTION

Accordingly, the present invention is directed to a direct single-step synthetic route to amidines of the formula (I), a key intermediate in PT coupler synthesis, via the addition of aminopyrazoles or 3-amino-4-substituted pyrazoles to organic nitriles.

DETAILED DESCRIPTION OF THE INVENTION

The present invention provides a direct access to a key intermediate amidine in PT coupler synthesis without forming moisture sensitive imidate intermediates. Moreover, the present invention reduces the number steps to synthesize such amidines from 2 to 1. Synthesis of N-(benzoxazol-2-yl)benzamidines by the condensation of benzonitriles and 2-aminobenzoxazoles is disclosed in the prior art (Subbaiah et al., *Synthesis*, May, 1990, pp. 422–424). However, a direct single-step synthesis involving 3-amino-4-substituted pyrazoles, 3-aminopyrazoles and organic nitriles is not disclosed or suggested in the prior art.

The process according to the present invention comprises reacting a compound of the formula (V), with a compound of the formula (III), in the presence of a condensing agent to obtain the compound of the formula (I):

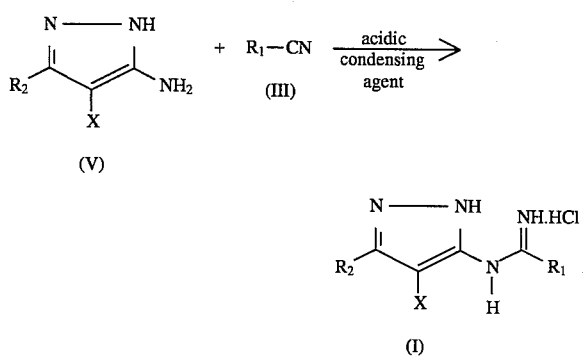

wherein X is a coupling-off group and $R_1$ and $R_2$ are independently hydrogen or a coupler substituent known in the photographic art which does not adversely affect the desired properties of the coupler.

The preparation of the amidine of formula (I) from the aminopyrazole of formula (V) and the nitrile of the formula (III) is conducted either in the absence of a solvent or in the presence of a solvent such as chlorobenzene, dichlorobenzene, and haloalkanes. While these solvents are preferred, other organic solvents which are inert with respect to the reactants and the product and which satisfactorily dissolve the subject materials can be employed.

Reaction temperatures are adjusted within the boiling point range of the solvents (when present). Preferred reaction temperatures are in the range of 100° C. to 150° C. with ambient pressure and a reaction time of 0.1 to 4 hours.

A condensing agent is necessary for the formation of amidine. Preferred condensing agents are anhydrous aluminum chloride, boron trifluoride, antimony pentafluoride, stannic chloride, and other acidic condensing agents known in the art.

The conversion of amidine to amidoxime followed by cyclization to afford the desired PT couplers (II) can be carried out by direct oxidation of the amidines (I) to produce the desired PT couplers.

In the generic structures (I) and (II), X is a coupling-off group known in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Additionally, formula (II) includes compounds wherein $R_1$ or $R_2$ is a reactive substituent which can be converted to the coupler substituent, thereby providing a dye-forming 1H-pyrazolo[1,5-b] [1,2,4]triazole coupler.

Representative classes of coupling-off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclicimido, thiocyano, alkylthio, arylthio, heterocyclylthio, suflonamido, phosphonyloxy and arylazo. They are described in, for example, U.S. Pat. Nos. 2,355,169; 3,227,551; 3,432,521; 3,476,563; 3,617,291; 3,880,661; 4,052,212; 4,540,654 and 4,134,766; in U.K. patents and published application numbers 1,466,728; 1,531,927; 1,533,039; 2,006,755A and 2,017,704A; and in EP 177,765; the disclosures of which are incorporated herein by reference. Examples of specific coupling-off groups are

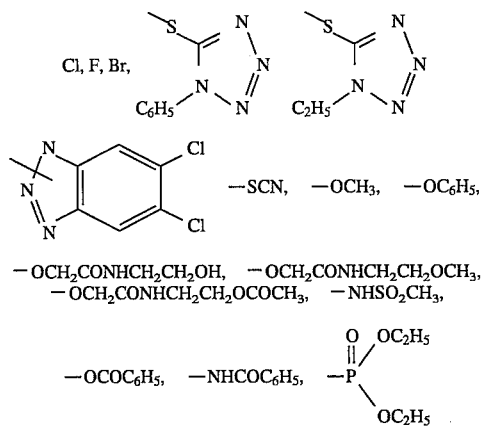

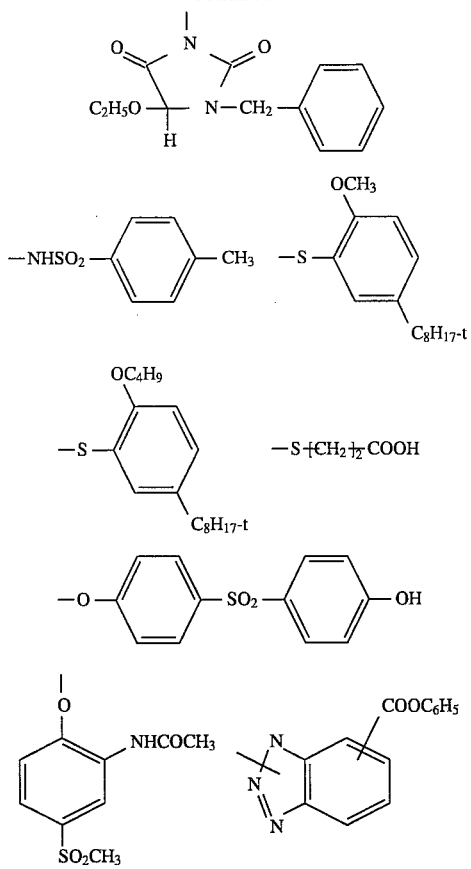

wherein X is chlorine, bromine or —S—Ar, and wherein Ar is an unsubstituted or substituted phenylene group. Compounds in which X is chlorine are preferred.

$R_1$ and $R_2$ each independently represent hydrogen or a coupler substituent known in the art which typically promotes solubility, diffusion resistance or dye hue or dye stability of the dye formed upon reaction of the coupler with the oxidized color developing agent. Examples of coupler substituent groups include an alkyl group which may be straight or branched, and which may be substituted, such as methyl, ethyl, n-propyl, n-butyl, t-butyl, trifluoromethyl, tridecyl or 3-(2,4,-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenlythio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N, N-dipropyl-sulfamoylamino or N-methyl-N-decylsulfamoylamino.

Additional examples of coupler substituent groups include a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycarbonylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy) acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group carbon atoms which may be substituted; a carboxyl group which may be substituted; a sulfo group which may be substituted; hydroxyl; an amino group which may be substituted; or a carbonamido group which may be substituted. Substituents for the above substituted $R^1$ or $R^2$ groups include those that do not adversely affect the desired properties of the pyrazolotriazole coupler. Representative substituents for the substituted $R_1$ or $R_2$ groups include halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group. Generally, the above groups and substituents thereof which contain an alkyl group may include an alkyl group having 1 to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

Preferably, $R_1$ or $R_2$ represents hydrogen, an alkyl group, an aryl group, a carbonamido group, a sulfonamido group, a sulfone group, a thio group, a sulfoxide group, a ureido group or a multicyclic group such as adamantlyl, camphoryl, norbornyl or a polynuclear aromatic.

Additionally, $R_1$ or $R_2$ in formula (I) may constitute a reactive group which can be converted to a coupler substituent as defined above, thereby providing a dye-forming 1H-pyrazolo[1,5-b] [1,2,4]triazole coupler. Thus, formula (I) includes compounds produced according to the method of the present invention which can be further modified through the R1 or R2 substituent to provide a desired dye-forming 1H-pyrazolo[1,5-b] [1,2,4]triazole coupler by methods known in the art. For example, when $R_1$ or $R_2$ is amino (—NH2), the amino can be reacted with a group such as $R_3$—CO—Cl, wherein $R_3$ is an alkyl, aryl, heterocyclic, alkoxy, aryloxy, alkylamino or arylamino group, to form a substituent of $R_3$—CO—NH— on the pyrazolotriazole ring. An example of such a method is illustrated in U.S. Pat. No. 4,540,654 the disclosure of which is incorporated herein by reference.

Additionally, the above-described $R_1$ or $R_2$ groups can be a ballast group, which is known in the photographic art as a radical of such size and configuration as to confer on the coupler molecules sufficient bulk to render the coupler substantially non-diffusible from the layer in which it is coated in a photographic element. Couplers of the invention may be attached to ballast groups, or to polymeric chains through one or more of the groups on the pyrazolotriazole nucleus. For example, one or more coupler moieties can be attached to the same ballast group.

Representative ballast groups include substituted or unsubstituted alkyl or alkoxy or aryloxy or aryl groups containing 8 to 32 carbon atoms. Representative substituents of the ballast groups include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents contain 1 to 30 carbon atoms and 6 to 30 carbon atoms, respectively. These ballast group substituents can be further substituted with the same substituents. Illustrative amidine compounds of the formula (I) which can be produced according to the present invention are as follows:

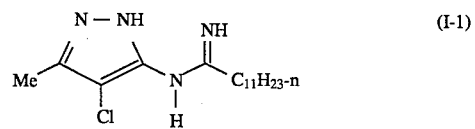

(I-1)

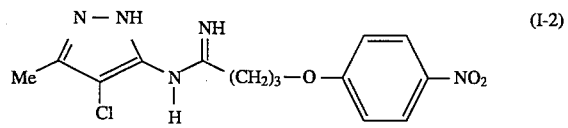

(I-2)

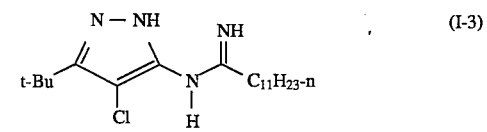

(I-3)

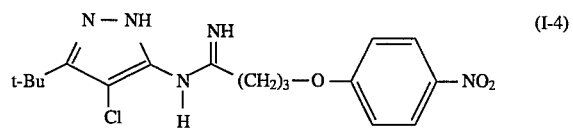

(I-4)

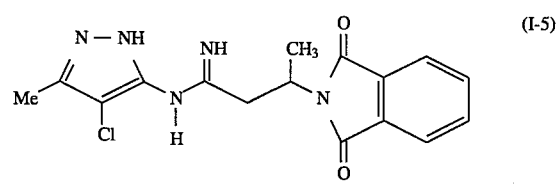

(I-5)

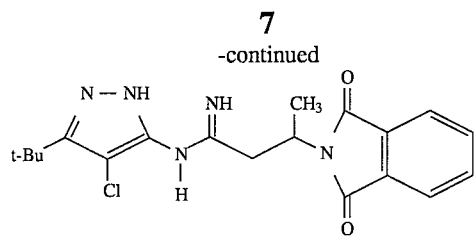

Each of the above compounds are useful intermediates for the magenta dye-forming couplers and each contains a ballast group for $R_1$ in the formula (I).

The present invention is more clearly described by, though in no way limited to, the following examples.

SYNTHESIS OF I-6

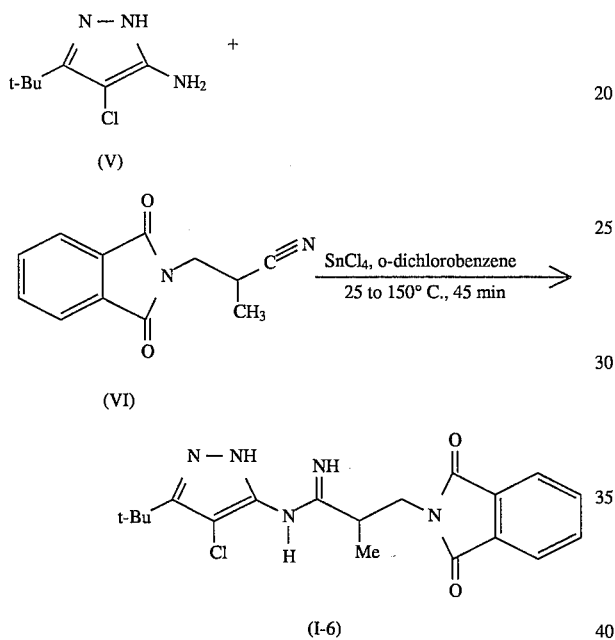

A 100-mL flask equipped with a magnetic stirring bar and a pressure equalizing addition funnel was heated under a dry stream of argon and allowed to cool to room temperature. The flask was charged with 3-amino-4-chloro-5-tert-butylpyrazole (2.0 g 11.52 mmol), pthaloyl blocked nitrile (VI, 2.59 g, 12.1 mmol), and dry o-dichlorobenzene as the solvent. The reaction flask was immersed in a water bath (≈25° C.) and anhydrous stannic chloride (1.75 mL, 3.9 g, 15 mmol) was added dropwise through a hypodermic syringe under argon; the reaction turned yellow. The contents of the flask were carefully heated (oil bath) to a temperature of 150° C. and maintained at that temperature until completion (30 min, TLC 9:2, $CH_2Cl_2$:MeOH) of the reaction.

The mixture was cooled and anhydrous ether (≈75 mL) was added. The white solid was filtered, washed with ether, and dried (4.99 g, >100%). A part (2.3 g) of the crude solid was subjected to flash chromatography to furnish 1.51 g (66% yield) of the desired amidine as pale yellow solid. Calcd. for $C_{19}H_{22}ClN_5O_2$: C, 58.84; H, 5.72; N, 18.06; Cl, 9.14. Found: C, 57.94; H, 5.76; N, 16.80; Cl, 9.56. $^1$H-NMR (300MHz, CDCl30 and field desorption mass spectra (FDMS) were consistent with the free amidine structure.

While the invention has been described in detail and with reference to specific embodiments thereof, it will be apparent to one skilled in the art that various changes and modifications can be made therein without departing from the spirit and scope of the invention.

What is claimed is:

1. A process for preparing a compound of formula (I)

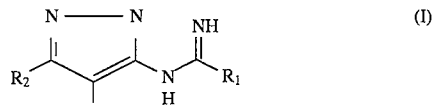

comprising reacting a compound of formula (V) with a compound of formula (III) in the presence of an acidic condensing agent as follows:

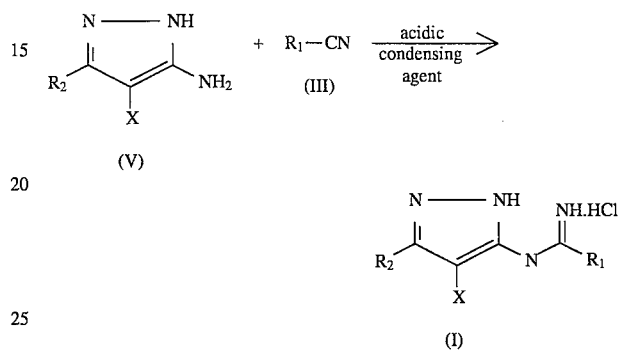

wherein, in each of the above structural formulae, $R_1$ is an alkyl group which be straight or branched and which may be substituted;

$R_2$ represents a member selected from the group consisting of hydrogen; alkyl which may be straight or branched and which may be substituted; alkoxy which may be substituted; alkylthio which may be substituted; aryl, aryloxy, and arylthio, each of which may be substituted; a heterocyclic group, a heterocyclic oxy group, and a heterocyclic thio group, each of which may be substituted and which contain a 3 to 7 membered heterocyclic ring composed of carbon atoms and at least one hetero atom selected from the group consisting of oxygen, nitrogen, and sulfur; cyano; an acyloxy group which may be substituted; a silyloxy group which may be substituted; a sulfonyloxy group which may be substituted; an acylamino group which may be substituted; an anilino group which may be substituted; an ureido group which may be substituted; an imido group which may be substituted; a sulfamoylamino group which may be substituted; an alkoxycarbonylamino group which may be substituted; an aryloxycarbonylamino group which may be substituted; a sulfonamido group which may be substituted; a carbamoyl group which may be substituted; an acyl group which may be substituted; a sulfonyl group which may be substituted; a sulfinyl group which may be substituted; an alkoxycarbonyl group which may be substituted; an aryloxycarbonyl group which may be substituted; an alkenyl group which may be substituted; a carboxyl group which may be substituted; a sulfo group which may be substituted; hydroxyl; an amino group which may be substituted; and a carbonamido group which may be substituted;

wherein the substituents of the $R_1$ and $R_2$ groups, if present, are selected from the group consisting of halogen; alkyl; aryl; aryloxy; heterocyclic, heterocyclic oxy, and heterocyclic thio wherein the heterocyclic moiety is a 3 to 7 membered heterocyclic ring composed of carbon atoms and at least one hetero atom selected from the group consisting of oxygen, nitrogen and sulfur; cyano; alkoxy; acyloxy; carbamoyloxy; silyloxy; sulfonyloxy; acylamino; anilino; ureido; imido; sulfonylamino; carbamoylamino; alkylthio; arylthio; alkoxycarbonylamino; aryloxycarbonylamino; sulfonamido; carbamoyl; acyl; sulfamoyl; sulfonyl; sulfinyl; alkoxycarbonyl; aryloxycarbonyl; alkenyl; carboxyl; sulfo; hydroxyl; amino; and carbonamido; and X is a coupling-off group.

2. A process according to claim 1, wherein X is selected from the group consisting of halogen, alkoxy, heterocyclyloxy, heterocyclic, sulfonyloxy, acyloxy, carbonamido, imido, acyl, heterocyclicimido, thiocyano, alkylthio, arylthio, heterocyclylthio, sulfonamido, phosphonyloxy, and arylazo.

3. The process as claimed in claim 2, wherein the reaction temperature is in the range of 100° C. to 150° C.

4. The process as claimed in claim 3, wherein $R_1$ or $R_2$ is a reactive substituent which can be converted into a coupler substituent and is a group of the formula $R_3$—CO—NH— wherein $R_3$ is selected from the group consisting of alkyl, aryl, heterocyclic, alkoxy, aryloxy, alkylamino, and arylamino.

5. A process for preparing a compound of formula (I)

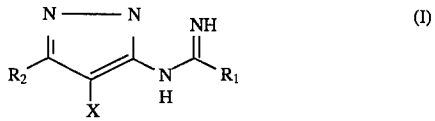

comprising reacting a compound of formula (V) with a compound of formula (III) in the presence of an acidic condensing agent as follows:

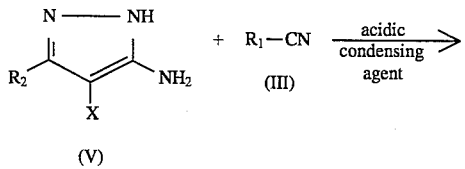

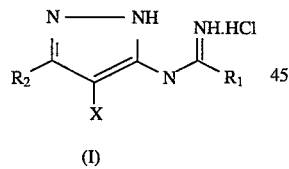

wherein, in each of the above structural formulae, $R_1$ is an alkyl group which may be straight or branched or a group of the formula:

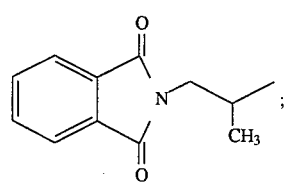

$R_2$ is an alkyl group which may be straight or branched; and

X is a halogen.

6. A process for preparing a compound of formula (I)

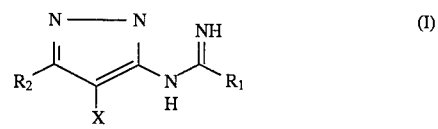

comprising reacting a compound of formula (V) with a compound of formula (III) in the presence of an acidic condensing agent as follows:

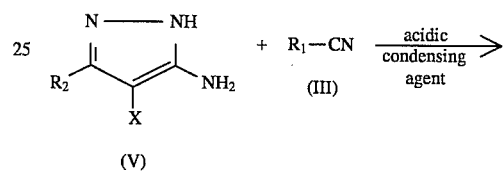

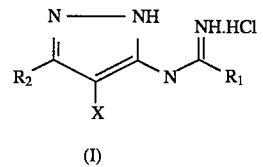

wherein, in each of the above structural formulae, $R_1$ is $C_{11}H_{23}$-n or

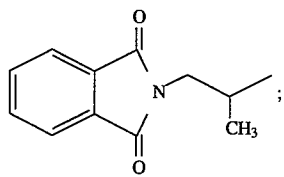

$R_2$ is t-butyl; and

X is chloro.

* * * * *